United States Patent
Harada et al.

(10) Patent No.: US 6,355,663 B1
(45) Date of Patent: Mar. 12, 2002

(54) SUBSTITUTED ISOXAZOLYLTHIOPHENE COMPOUNDS

(75) Inventors: Masahiro Harada; Junko Takeda; Toshio Nakamura; Shiuji Saito, all of Tokyo (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 09/786,119

(22) PCT Filed: Sep. 29, 1999

(86) PCT No.: PCT/JP99/05315

§ 371 Date: Mar. 1, 2001

§ 102(e) Date: Mar. 1, 2001

(87) PCT Pub. No.: WO00/18765

PCT Pub. Date: Apr. 6, 2000

(30) Foreign Application Priority Data

Sep. 30, 1998 (JP) ............................................ 10-276288

(51) Int. Cl.[7] ....................... C07D 413/04; A61K 31/42
(52) U.S. Cl. ......................................... 514/378; 548/240
(58) Field of Search ............................ 548/240; 514/378

(56) References Cited

FOREIGN PATENT DOCUMENTS

WO         200004578     *   8/2000   ................ 548/240

* cited by examiner

Primary Examiner—Robert Gerstl
(74) Attorney, Agent, or Firm—Lorusso & Loud

(57) ABSTRACT

This invention provides a substituted isoxazolylthiophene compound represented by the formula

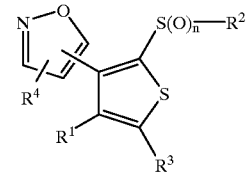

wherein $R^1$ and $R^2$ individually represent an alkyl group of 1–5 carbon atoms, $R^3$ represents a cyano group or a group $CONR^5R^6$ (in which $R^5$ and $R^6$ individually represent a hydrogen atom or an alkyl group of 1–10 carbon atoms), $R^4$ represents an alkyl group of 1–5 carbon atoms or a phenyl group, and n is an integer of 0–2, or a salt thereof.

The compounds of the invention are useful for the treatment or prevention of various bone diseases or nerve diseases, because they specifically enhance the action of the cell differentiation induction factors found in a living body.

4 Claims, No Drawings

SUBSTITUTED ISOXAZOLYLTHIOPHENE COMPOUNDS

TECHNICAL FIELD

This invention relates to a novel substituted isoxazolylthiophene compound and a pharmaceutical composition comprising the same as an active ingredient, which is useful for enhancing the action of cell differentiation induction factors.

BACKGROUND ART

Compounds which have been reported as being therapeutically or prophylactically effective against bone diseases or nerve diseases by enhancing the action of the cell differentiation induction factors present in or administered to a living body include fused thiophene derivatives disclosed in WO98/09958, but no such report covers the compounds of the present invention.

DISCLOSURE OF INVENTION

We extensively studied and found that certain substituted isoxazolylthiophene compounds are effective for treatment or prevention of bone diseases or nerve diseases, and finally completed the invention.

More specifically, the present invention is directed to a substituted isoxazolylthiophene compound represented by the formula (I)

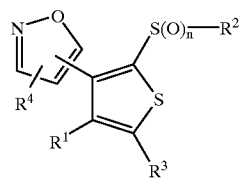

wherein $R^1$ and $R^2$ individually represent an alkyl group of 1–5 carbon atoms, $R^3$ represents a cyano group or a group $CONR^5R^6$ (in which $R^5$ and $R^6$ individually represent a hydrogen atom or an alkyl group of 1–10 carbon atoms), $R^4$ represents an alkyl group of 1–5 carbon atoms or a phenyl group, and n is an integer of 0–2, or a salt thereof.

The alkyl group of 1–5 carbon atoms used herein means a straight or branched alkyl group and includes, for example, a methyl group, an ethyl group, an n-propyl group, an isopropyl group, an n-butyl group, an isobutyl group and an n-pentyl group.

The alkyl group of 1–10 carbon atoms as used herein means a straight or branched alkyl group and includes, for example, a methyl group, an ethyl group, an n-propyl group, an isopropyl group, an n-butyl group, an isobutyl group, an n-pentyl group, an n-hexyl group and an n-octyl group.

The salt as used herein may include salts with pharmaceutically acceptable acids (such as hydrochloric acid, sulfuric acid, nitric acid, tartaric acid, citric acid, maleic acid, fumaric acid, etc.), as well as their hydrates.

The invention may further encompass the compounds which are capable of producing the active compounds of this invention through in vivo metabolism after administration, or the compounds which are capable of producing the active compounds per se as produced by the metabolism of the compounds of the invention through in vivo metabolism.

The compounds (I) of the invention may be prepared, for example, according to the following processes:
1) The compounds (I) wherein $R^3$ is a cyano group and n is 0 may be prepared, for example, according to the process as illustrated by Reaction Scheme 1.

Reaction Scheme 1

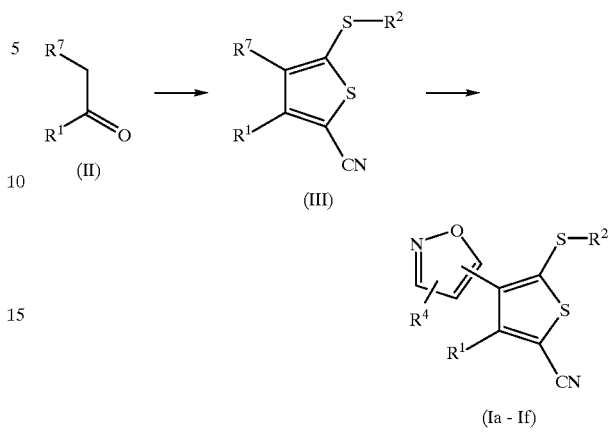

In the Reaction Scheme 1, $R^1$ and $R^2$ have the same meanings as defined above, and $R^7$ is a group $COCH_3$, $COCH_2R^4$ or $CH_2COR^4$ (wherein $R^4$ has the same meaning as defined above).

The Reaction Scheme 1 will be explained in detail below.
1)-(1) The present compounds (Ia) and (Ib) may be prepared using as a starting material the diketone compound (II) wherein $R^7$ represents $COCH_3$.

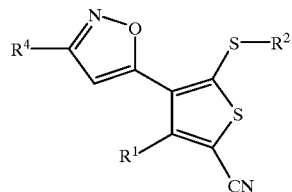

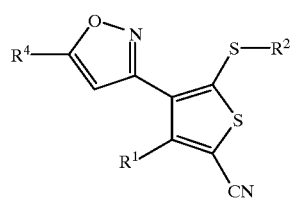

More specifically, the diketone compound (II) wherein $R^7$ represents $COCH_3$ may be condensed with carbon disulfide ($CS_2$) in the presence of a base and then the resulting condensed product may be converted to the thiophene compound (III) wherein $R^7$ represents $COCH_3$ by thioetherification of one of the sulfur atoms derived from carbon disulfide with a haloacetonitrile such as chloroacetonitrile or bromoacetonitrile and the remaining sulfur atom with $R^2$—$X^1$ (wherein $R^2$ has the same meaning as defined above and $X^1$ is a leaving group such as a halogen atom, e.g., a chlorine atom or a bromine atom or a methylsulfoxy group), simultaneously with intramolecular cyclization reaction.

The base which may be used in this reaction may include alkali metal hydroxides (lithium hydroxide, sodium hydroxide, potassium hydroxide, etc.), alkali metal carbonates (lithium carbonate, sodium carbonate, potassium carbonate, etc.), alkali metal hydrogencarbonates (sodium hydrogencarbonate, potassium hydrogencarbonate, etc.), alkali metal hydrides (sodium hydride, potassium hydride, etc.), inorganic bases (metallic sodium, metallic potassium, sodium amide, etc.), alkali metal alkoxides (sodium methoxide, sodium ethoxide, potassium t-butoxide, etc.), organic bases (triethylamine, diisopropylethylamine, tri-n-butylamine, 1,5-diazabicyclo[4.3.0]-5-nonene, 1,8-diazabicyclo[5.4.0]-7-undecene, pyridine, N,N-dimethylaminopyridine, etc.), organometallic compounds (n-butyl lithium, s-butyl lithium, t-butyl lithium, lithium diisopropylamide, sodium bis(trimethylsilyl)amide, etc.) and the like.

The reaction may be carried out in the presence or absence of a solvent. The solvent which may be used includes methanol, ethanol, n-propanol, isopropanol, n-butanol, t-butanol, dioxane, tetrahydrofuran, diethyl ether, petroleum ether, n-hexane, cyclohexane, benzene, toluene, xylene, chlorobenzene, pyridine, ethyl acetate, N,N-dimethylformamide, dimethyl sulfoxide, dichloromethane, chloroform, carbon tetrachloride, water and the like.

The base and solvent to be used, as well as use or no use of the solvent should be properly selected depending on the substrates and reaction parameters used in the reaction.

Then, $R^7$ of the thiophene compound (III) wherein $R^7$ is a group $COCH_3$ is condensed with an activated carboxylic acid derivative represented by $R^4$—COOH (wherein $R^4$ has the same meaning as above) such as an alkyl ester, e.g., methyl ester or ethyl ester or an acid halide or an acid anhydride, to convert $R^7$ to a group $COCH_2COR^4$. Subsequent condensed cyclization reaction using hydroxylamine or a derivative thereof may produce the compound (Ia) or (Ib) of this invention.

This condensation reaction is preferably carried out in the presence of a base. The base which may be used in this reaction includes alkali metal hydroxides (lithium hydroxide, sodium hydroxide, potassium hydroxide, etc.), alkali metal carbonates (lithium carbonate, sodium carbonate, potassium carbonate, etc.), alkali metal hydrogencarbonates (sodium hydrogencarbonate, potassium hydrogencarbonate, etc.), alkali metal hydrides (sodium hydride, potassium hydride, etc.), inorganic bases (metallic sodium, metallic potassium, sodium amide, etc.), alkali metal alkoxides (sodium methoxide, sodium ethoxide, potassium t-butoxide, etc.), organic bases (triethylamine, diisopropylethylamine, tri-n-butylamine, 1,5-diazabicyclo[4.3.0]-5-nonene, 1,8-diazabicyclo[5.4.0]-7-undecene, pyridine, N,N-dimethylaminopyridine, etc.), organometallic compounds (n-butyl lithium, s-butyl lithium, lithium diisopropylamide, sodium bis(trimethylsilyl)amide, etc.) and the like.

The reaction may be carried out in the presence or absence of a solvent. The solvent which may be used includes methanol, ethanol, n-propanol, isopropanol, n-butanol, t-butanol, dioxane, tetrahydrofuran, diethyl ether, petroleum ether, n-hexane, cyclohexane, benzene, toluene, xylene, chlorobenzene, pyridine, ethyl acetate, N,N-dimethylformamide, dimethyl sulfoxide, dichloromethane, chloroform, carbon terachloride, water and the like.

The hydroxylamine which is used for condensed cyclization reaction may be in the form of a salt with hydrochloric acid, sulfuric acid or the like, and the reaction is preferably carried out in the presence of a base. The bases which may be used in this reaction include alkali metal hydroxides (lithium hydroxide, sodium hydroxide, potassium hydroxide, etc.), alkali metal carbonates (lithium carbonate, sodium carbonate, potassium carbonate, etc.), alkali metal hydrogencarbonates (sodium hydrogencarbonate, potassium hydrogencarbonate, etc.), alkali metal hydrides (sodium hydride, potassium hydride, etc.), inorganic bases (metallic sodium, metallic potassium, sodium amide, etc.), alkali The reagent and solvent to be used, as well as use or no use of the solvent should be properly selected for each of these reactions, depending on the substrates and reaction parameters used.

1)-(2) The compounds (Ic–If) of the invention may be prepared according to the Reaction Scheme 1 using as a starting material the diketone compound (II) wherein $R^7$ represents $COCH_2R^4$ or $CH_2COR^4$.

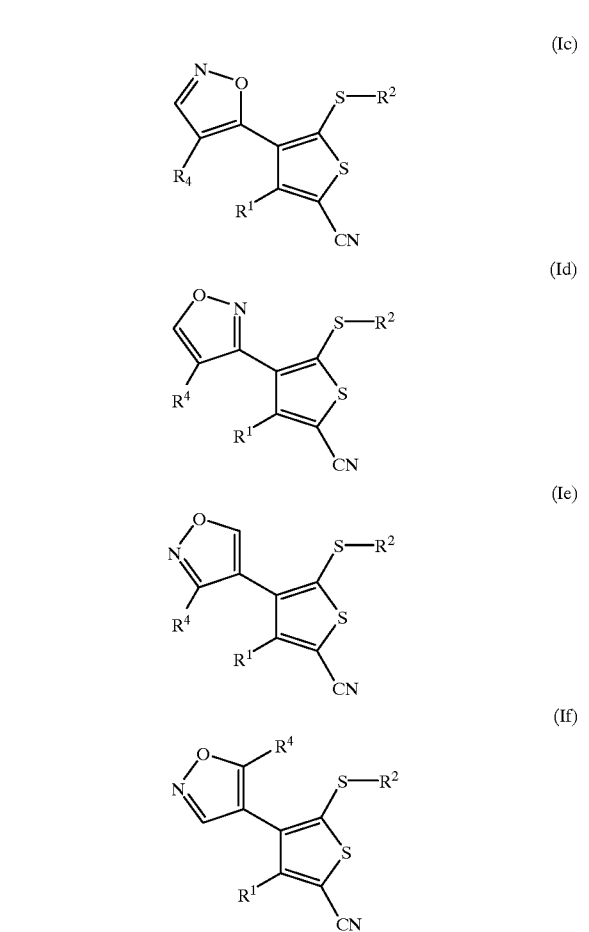

More specifically, the thiophene compound (III) wherein $R^7$ represents $COCH_2R^4$ or $CH_2COR^4$ may be prepared according to the process of 1)-(1) using the diketone compound (II) wherein $R^7$ represents a group $COCH_2R^4$ or $CH_2COR^4$.

The compounds (Ic–If) of the invention may be prepared by converting $R^7$ of the thiophene compound (III) wherein R⁷ represents a group COCH₂R⁴ or CH₂COR⁴ to formyl, halomethylene, alkoxymethylene or aminomethylene, followed by subsequent condensed cyclization reaction using hydroxylamine or a derivative thereof.

The formylation reaction may be carried out by a process wherein a formyl ester such as methyl formate or ethyl formate or carbon monooxide is condensed in the presence of a base, or a process wherein the carbonyl group of R⁷ is converted to an enamine with secondary amine such as dimethylamine, pyrrolidine or morpholine followed by the reaction with an N,N-dimethylformamide derivative such as N,N-dimethylformamide, N,N-dimethylformamide dimethyl acetal or t-butoxy(dimethylamino)methane in the presence of 10 phosgene, phosphorus oxychloride, oxalyl chloride or the like.

The aminomethylene-forming reaction may be carried out using an N,N-dimethylformamide derivative such as N,N-dimethylformamide, N,N-dimethylformamide dimethyl acetal or t-butoxy(dimethylamino)methane.

The halomethylene-forming reaction may be carried out by converting the carbonyl group of R⁷ to an enamine with a secondary amine such as dimethylamine, pyrrolidine or morpholine and subsequent reaction with a haloform such as chloroform in the presence of a base.

The alkoxymethylene-forming reaction may be carried out by heating in the presence of an alkyl orthoformate such as methyl orthoformate or ethyl orthoformate and acetic anhydride.

The aminomethylene-forming reaction may be carried out using an N,N-dimethylformamide derivative such as N,N-dimethylformamide dimethyl acetal or t-butoxy(dimethylamino)methane.

The bases which may be used in the formylation and the halomethylene-forming reaction include alkali metal hydroxides (lithium hydroxide, sodium hydroxide, potassium hydroxide, etc.), alkali metal carbonates (lithium carbonate, sodium carbonate, potassium carbonate, etc.), alkali metal hydrogencarbonates (sodium hydrogencarbonate, potassium hydrogencarbonate, etc.), alkali metal hydrides (sodium hydride, potassium hydride, etc.), inorganic bases (metallic sodium, metallic potassium, etc.), alkali metal acetate (sodium acetate, etc.), alkali metal alkoxides (sodium methoxide, sodium ethoxide, potassium t-butoxide, etc.), organic bases (triethylamine, diisopropylethylamine, tri-n-butylamine, 1,5-diazabicyclo[4.3.0]-5-nonene, 1,8-diazabicyclo[5.4.0]-7-undecene, pyridine, N,N-dimethylaminopyridine, etc.), organometallic compounds (n-butyl lithium, s-butyl lithium, t-butyl lithium, lithium diisopropylamide, sodium bis(tri-methylsilyl)amide, etc.) and the like.

The formylation reaction, halomethylene-forming reaction, alkoxymethylene-forming reaction and aminomethylene-forming reaction may be carried out in the presence or absence of a solvent. The solvent which may be used includes methanol, ethanol, n-propanol, isopropanol, n-butanol, t-butanol, dioxane, tetrahydrofuran, diethyl ether, petroleum ether, n-hexane, cyclohexane, benzene, toluene, xylene, chlorobenzene, pyridine, ethyl acetate, N,N-dimethylformamide, dimethyl sulfoxide, dichloromethane, chloroform, carbon tetrachloride, water and the like.

The reagent and solvent to be used in each of the reactions, as well as use or no use of the solvent, should be properly selected, depending on the substrates and reaction parameters used.

2) The compound (Ig) of the invention, which is the compound (I) wherein R³ represents a group CONR⁵R⁶ (wherein R⁵ and R⁶ have the same meanings as defined above) and n is 0, may be prepared by hydrolysis of the cyano group of the compounds (Ia–If) under acidic or basic conditions.

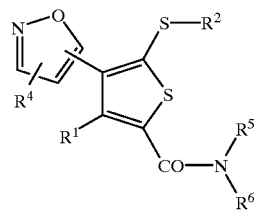

(Ig)

The hydrolysis reaction in this reaction may be carried out according to a conventional reaction for hydrolysis of a nitrile group; for example, acid hydrolysis using hydrochloric acid, sulfuric acid, acetic acid, phosphoric acid, polyphosphoric acid, etc. alone or in any optional combination therewith, and alkaline hydrolysis using lithium hydroxide, sodium hydroxide, potassium hydroxide, lithium carbonate, sodium carbonate, potassium carbonate, sodium hydrogencarbonate, potassium hydrogencarbonate, ammonia, etc.

The reaction may be carried out in the presence or absence of a solvent. The solvent which may be used includes methanol, ethanol, n-propanol, isopropanol, n-butanol, t-butanol, dioxane, tetrahydrofuran, diethyl ether, petroleum ether, n-hexane, cyclohexane, benzene, toluene, xylene, chlorobenzene, pyridine, ethyl acetate, N,N-dimethylformamide, dimethyl sulfoxide, dichloromethane, chloroform, carbon tetrachloride, water and the like.

The reagent and solvent to be used in the reaction, as well as use or no use of the solvent, should be properly selected, depending on the substrates and reaction parameters used.

The compound (Ig) may be prepared according to the following process:

The thiophene compounds (III) having an alkoxycarbonyl group instead of the cyano group may be prepared by using a halogenated acetic acid ester such as methyl bromoacetate or ethyl bromoacetate instead of the haloacetonitrile such as chloroacetonitrile or bromoaceto -nitrile, which was used, in the above 1)-(1), for thioetherification of one of the sulfur atoms derived from carbon disulfide in the preparation step of the intermediate thiophene compounds (III) for the compounds (Ia–If).

Then, the alkoxycarbonyl group of the thiophene compound (III) is hydrolyzed to a carboxyl group under acidic or basic conditions, followed by condensed cyclization reaction using hydroxylamine to prepare the compounds (Ia–If) having a carboxyl group instead of the cyano group as in the above 1).

The above-mentioned hydrolysis may be carried out by a conventional reaction for hydrolyzing an ester; for example, acid hydrolysis using hydrochloric acid, sulfuric acid, acetic acid, phosphoric acid, polyphosphoric acid, etc. alone or in any optional combination therewith, and alkaline hydrolysis using lithium hydroxide, sodium hydroxide, potassium hydroxide, lithium carbonate, sodium carbonate, potassium carbonate, sodium hydrogencarbonate, potassium hydrogencarbonate, ammonia, etc.

This reaction may be carried out in the presence or absence of a solvent. The solvent which may be used includes methanol, ethanol, n-propanol, isopropanol, n-butanol, t-butanol, dioxane, tetrahydrofuran, diethyl ether, petroleum ether, n-hexane, cyclohexane, benzene, toluene, xylene, chlorobenzene, pyridine, ethyl acetate, N,N-dimethylformamide, dimethyl sulfoxide, dichloromethane, chloroform, carbon tetrachloride, water and the like.

The reagent and solvent to be used in the reaction, as well as use or no use of the solvent should be properly selected, depending on the substrates and reaction parameters used.

Amidation of the carboxyl group with an amino compound represented by $HNR^5R^6$ (wherein $R^5$ and $R^6$ have the same meanings as defined above) may finally give the compound (Ig) of the invention.

Amidation includes transesterification with an amine, a condensation reaction of a carboxylic acid derived from hydrolysis of an ester with an amine or the like. A condensing agent includes, for example, acid halides such as thionyl chloride, alkyl chlorocarbonates such as ethyl chlorocarbonate, carbodiimide compounds such as dicyclohexylcarbodiimide, 1-ethyl-3-(3-dimethylamino)propylcarbodiimide, sulfonyl chloride compounds such as methanesulfonyl chloride, phosphorus compounds such as diphenyl phosphite, diphenylphosphoryl chloride, triphenylphosphine-diethyl azadicarboxylate, N,N'-carbodiimidazole.

This reaction may be carried out in the presence or absence of a solvent. The solvent which may be used includes methanol, ethanol, n-propanol, isopropanol, n-butanol, t-butanol, dioxane, tetrahydrofuran, diethyl ether, petroleum ether, n-hexane, cyclohexane, benzene, toluene, xylene, chlorobenzene, pyridine, ethyl acetate, N,N-dimethylformamide, dimethyl sulfoxide, dichloromethane, chloroform, carbon tetrachloride, water and the like.

The reagent and solvent to be used in the reaction, as well as use or no use of the solvent should be properly selected, depending on the substrates and reaction parameters used.

3) The compounds (I) of the invention wherein n is 1 or 2 may be prepared by using a conventional oxidation reaction to oxidize the sulfur atom in the alkylthio group (—S—R 2) of the compounds (Ia–Ig) to sulfoxide or sulfone. The oxidizing agent which may be used for the oxidation reaction includes, for example, hydrogen peroxide, t-butyl hydroperoxide, meta-chloroperbenzoic acid, peracetic acid, sodium meta-periodate, bromous acid sodium salt, sodium hypochlorite, periodobenzene, and the like.

This reaction may be carried out in the presence or absence of a solvent. The solvent which may be used includes methanol, ethanol, n-propanol, isopropanol, n-butanol, t-butanol, dioxane, tetrahydrofuran, diethyl ether, petroleum ether, n-hexane, cyclohexane, benzene, toluene, xylene, chlorobenzene, pyridine, ethyl acetate, N,N-dimethylformamide, dimethyl sulfoxide, dichloromethane, chloroform, carbon tetrachloride, water and the like.

The reagent and solvent to be used in the reaction, as well as use or no use of the solvent should be properly selected, depending on the substrates and reaction parameters used.

The compound of the present invention has a potent enhancing activity of osteogenesis and can be used as an enhancing agent for osteogenesis in repairing or transplanting the bone or alveolar bone, alone or in admixture with a carrier for bone repairing.

The compound of the invention, when used as an enhancing agent for osteogenesis, may be administered orally or parenterally in a dosage form of tablets, powders, solutions, injections, suppositories or others. It may also be directly applied to the bone that has been surgically removed. Optimum dose may be chosen by totally considering the age, sexuality, body weight and others of patients.

The compound of the invention, when used in admixture with a carrier for bone repairing, may be adhered onto or included in an artificial bone made of metals, ceramics or polymers. The artificial bone is preferably made to have porous surface so as to release the enhancing agent of osteoblast differentiation according to the invention in living tissues when the bone is transplanted to the defective part of bone.

BEST MODE FOR CARRYING OUT THE INVENTION

The invention will be more fully explained by way of the following Examples and Test Examples.

EXAMPLE 1

3,4'-Dimethyl-4-(isoxazol-5-yl)-5-(methylthio)thiophene-2-carboxamide a) Ethyl 3-methyl-5-methylthio-4-propionylthiophene-2-carboxylate To a dimethyl sulfoxide (88 ml) solution containing 2,4-hexanedione (10.0 g, 87.6 mmol) were added dropwise under ice-cooling an 85% solution containing potassium hydroxide (13.6 g, 175.2 mmol) in water (8 ml) and carbon disulfide (7.3 g, 96.4 mmol) in turn, and then the mixture was stirred at that temperature for 30 minutes. Subsequently, a solution containing ethyl bromoacetate (13.2 g, 78.8 mmol) in dimethyl sulfoxide (8 ml) was added dropwise under ice-cooling, the mixture was stirred at that temperature for 30 minutes. Then methyl iodide (12.4 g, 87.6 mmol) was added, and the mixture was stirred further for 20 minutes. The reaction solution was extracted with ethyl acetate, and the organic layer was washed (with water and saturated aqueous sodium chloride, in turn), dried (over anhydrous magnesium sulfate), filtered and concentrated under reduced pressure.

The resulting residue was then dissolved in N,N-dimethylformamide (80 ml), anhydrous potassium carbonate (12.1 g, 87.6 mmol) was added and the mixture was stirred at room temperature for 10 hours. To the reaction solution was added water, the precipitate was filtered, washed (with water), dried and then recrystallized from ethyl acetate -n-hexane to afford ethyl 3-methyl-5-methylthio-4-propionylthiophene-2-carboxylate (7.3 g, 31%) as colorless crystals.

Melting point: 114.0–115.0° C.

b) 3,4'-Dimethyl-4-(isoxazol-5-yl)-5-(methylthio)thiophene-2-carboxylic acid

To 60% sodium hydride (2.14 g, 53.6 mmol) which had been washed three times with n-hexane (5 ml) were added at room temperature in turn ethyl formate (22 ml) and a solution of ethyl 3-methyl-5-methylthio-4-propionylthiophene-2-carboxylate (7.0 g, 25.7 mmol) in tetrahydrofuran (54 ml), and the mixture was then heated at 80° C. with stirring for one hour. The reaction solution was allowed to cool down to room temperature and made acidic by addition of a saturated aqueous solution of ammonium chloride, extracted with ethyl acetate, and the organic layer was washed with water, dried (over anhydrous magnesium sulfate) and concentrated under reduced pressure.

To the resulting residue were added ethanol (22 ml) and a 6N aqueous sodium hydroxide solution (7.3 ml) and the mixture was heated at 60° C. with stirring for one hour. The reaction solution was allowed to cool down to room temperature and made acidic by addition of 3N hydrochloric acid, extracted with ethyl acetate, and the organic layer was washed with water, dried (over anhydrous magnesium sulfate) and concentrated under reduced pressure.

To the resulting residue were added pyridine (11 ml) and hydroxylamine hydrochloride (1.83 g, 26.4 mmol) and the mixture was heated at 80° C. with stirring for one hour. The reaction solution was cooled, diluted with water, then made acidic by addition of 12N hydrochloric acid and extracted with ethyl acetate. The organic layer was washed (with water and saturated aqueous sodium chloride, in turn), dried (over anhydrous magnesium sulfate), and concentrated under reduced pressure to give crude crystals, which were then recrystallized from ethyl acetate -n-hexane to afford 3,4'-dimethyl-4-(isoxazol-5-yl)-5-(methylthio)thiophene-2-carboxylic acid (5.56 g, 80%) as colorless crystals.

Melting point: 190.0–191.5° C.

c) 3,4'-Dimethyl-4-(isoxazol-5-yl)-5-(methylthio) thiophene -2-carboxamide

To tetrahydrofuran (15 ml) containing 3,4'-dimethyl-4-(isoxazol-5-yl)-5-(methylthio)thiophene-2-carboxylic acid (4.13 g, 15.3 mmol) were added at room temperature N,N-dimethylformamide (0.5 ml) and thionyl chloride (2.0 g, 16.9 mmol). After stirring the mixture for 20 minutes, 25% aqueous ammonia (10 ml) was added thereto and the reaction solution was extracted with ethyl acetate. The organic layer was then washed (with water and aqueous saturated sodium chloride, in turn), dried (over anhydrous magnesium sulfate) and concentrated under reduced pressure. The residue thus obtained was purified by silica gel column chromatography (developing solvent: n-hexane/ethyl acetate= 1:1) and recrystallized from diethyl ether-n-hexane to afford 3,4'-dimethyl-4-(isoxazol-5-yl)-5-(methylthio)thiophene-2-carboxamide (2.19 g, 53%) as a colorless crystals.

Melting point: 140.0–141.0° C.

EXAMPLE 2

3-Ethyl-4-(4-methylisoxazol-5-yl)-5-(methylthio) thiophene-2-carbonitrile a) 3-Ethyl-5-methylthio-4-propionylthiophene-2-carbonitrile To a solution containing 2,4-heptanedione (10.0 g, 78.0 mmol) in dimethyl sulfoxide (100 ml) were added dropwise under ice-cooling an 85% solution containing potassium hydroxide (10.3 g, 156.0 mmol) in water (10 ml) and carbon disulfide (5.9 g, 78.0 mmol) in turn, and then the mixture was stirred at that temperature for 30 minutes. Subsequently, a solution containing chloroacetonitrile (5.3 g, 70.2 mmol) in dimethyl sulfoxide (10 ml) was added dropwise under ice-cooling over 5 minutes and the mixture was stirred at that temperature for 20 minutes. Potassium carbonate (10.8 g, 78.0 mmol) and methyl iodide (12.2 g, 85.8 mmol) were then added and the mixture was stirred further for 30 minutes. The reaction solution was extracted 10 with ethyl acetate, and the organic layer was washed (with water and aqueous saturated sodium chloride, in turn), dried (over anhydrous magnesium sulfate), filtered and concentrated under reduced pressure. The residue thus obtained was purified by silica gel column chromatography (developing solvent: n-hexane/ethyl acetate=10:1) and the crystals thus obtained were washed with n-hexane to afford 3-ethyl-5-methylthio-4-propionylthiophene-2-carbonitrile (14.8 g, 88%) as colorless prisms.

Melting point: 66.0–67.0° C.

b) 3-Ethyl-4-(4-methylisoxazol-5-yl)-5-(methylthio)-thiophene-2-carbonitrile

To a suspension containing sodium methoxide (1.08 g, 20.0 mmol) in benzene (20 ml) were added in turn ethyl formate (1.48 g, 20.0 mmol) and a solution of ethyl 3-ethyl-5-methylthio-4-propionylthiophene-2-carboxylate (2.39 g, 10.0 mmol) in benzene (20 ml) at room temperature, and the mixture was then stirred at room temperature for 30 minutes. Then, a solution containing ethyl formate (1.48 g, 20.0 mmol) in tetrahydrofuran (20 ml) was added and the mixture was stirred further for 16 hours. The reaction solution was washed (with 3N hydrochloric acid, water and aqueous saturated sodium chloride, in turn), dried (over anhydrous magnesium sulfate) and concentrated under reduced pressure.

To the resulting residue were added pyridine (20 ml) and hydroxylamine hydrochloride (0.76 g, 11.0 mmol) and the mixture was heated at 80° C. with stirring for 45 minutes. The reaction solution was allowed to cool down to room temperature, diluted with water and then extracted with ethyl acetate. The organic layer was washed (with water and saturated aqueous sodium chloride, in turn), dried (over anhydrous magnesium sulfate), concentrated under reduced pressure. The residue thus obtained was purified by silica gel column chromatography (developing solvent: n-hexane/ ethyl acetate=4:1–3:1) to afford 3-ethyl-4-(4-methylisoxazol-5-yl)-5-(methylthio)thiophene-2-carbonitrile (0.87 g, 33%) as a yellow oily substance. NMR (200MHz, CDCl$_3$) δ: 1.08 (t, 3H, J=7.5Hz), 2.01 (s, 3H), 2.55 (s, 3H), 2.66 (q, 2H, J=7.5Hz), 8.22 (s, 1H)

EXAMPLE 3

3-Ethyl-4-(4-methylisoxazol-5-yl)-5- (methylthio) thiophene-2-carboxamide

To 3-ethyl-4-(4-methylisoxazol-5-yl)-5-(methylthio) thiophene-2-carbonitrile (0.87 g, 3.3 mmol) was added conc. sulfuric acid (11 ml) and the mixture was heated at 60° C. for 1.5 hours. The reaction solution was allowed to cool down to room temperature, ice was added and then the mixture was extracted with ethyl acetate. The organic layer was washed (with water, saturated aqueous sodium hydrogen-carbonate and saturated aqueous sodium chloride, in turn), dried (over anhydrous magnesium sulfate) and concentrated under reduced pressure. The residue thus obtained was purified by silica gel column chromatography (developing solvent: chloroform/ ethyl acetate=1:0–3:1) and recrystallized from diethyl ether to afford 3-ethyl-4-(4-methylisoxazol-5-yl)-5-(methylthio)thiophene-2-carboxamide (0.39 g, 42%) as colorless crystals.

Melting point: 93.5–94.5° C.

EXAMPLE 4

4-(4-Methylisoxazol-5-yl)-5-methylthio-3-(1-propyl) -thiophene-2-carboxamide

According to the process as stated in Example 1 except for using 3,5-octanedione instead of the 2,4-hexanedione as a starting material, the title compound was prepared as a colorless oily substance.

NMR (200MHz, CDCl$_3$) δ: 0.84 (t, 3H, J=7.8Hz), 1.49 (dq, 2H, J=7.8Hz, 7.8Hz), 1.99 (s, 3H), 2.51 (s, 3H), 2.71 (t, 2H, 7.8 Hz), 5.85 (br.s, 2H), 8.23 (s, 1H)

EXAMPLE 4

3-Isopropyl-4-(4-methylisoxazol-5-yl)-5-(methylthio)-thiophene-2-carboxamide

According to the process as stated in Example 1 except for using 2-methyl-3,5-heptanedione instead of the 2,4-hexanedione as a starting material, and by carrying out recrystallization from diethyl ether - n-hexane, the title compound was prepared.

Melting point: 105.0° C.

EXAMPLE 5

3,4'-Dimethyl-5-ethylthio-4-(isoxazol-5-yl) thiophene-2-carboxamide

According to the processes as stated in Example 2 and Example 3 except for using ethyl bromide instead of the methyl iodide used in Example 2, the title compound was prepared as colorless needles.

Melting point: 120.0–121.0° C.

(Recrystallization solvent: Ethyl acetate-n-hexane).

EXAMPLE 6

3,4'-Dimethyl-5-isopropylthio-4-(isoxazol-5-yl) thiophene-2-carboxamide

According to the processes as stated in Example 2 and Example 3 except for using isopropyl iodide instead of the methyl iodide used in Example 2, the title compound was prepared as colorless crystals.

Melting point: 108.0–109.0° C.

(Recrystallization solvent: Diethyl ether-n-hexane)

EXAMPLE 7

3-Ethyl-4-(4-methylisoxazol-5-yl)-5-(methylthio) thiophene-2-carboxamide -4-(4-Etkylisoxazol-5-yl)-3-methyl-5-(methylthio)-thiophene-2-carboxamide.

According to the process as stated in Example 1 except for using 2,4-heptanedione instead of the 2,4-hexanedione as a starting material, the title compound was prepared as colorless crystals.

Melting point: 136.5–138.0° C.

(Recrystallization solvent: Diethyl ether)

EXAMPLE 8

4-(1- Butyl)isoxazol-5-yl]-3-methyl-5-(methylthio) -thiophene-2-carboxamide

According to the process as stated in Example 1 except for using 2,4-nonanedione instead of the 2,4-hexanedione as a starting material, the title compound was prepared as a colorless oily substance.

NMR (200 MHz, CDCl$_3$) δ: 0.87 (t, 3H, J=6.2Hz), 1.20–1.61 (m, 5=4H), 2.28–2.65 (m, 2H), 2.30 (s, 3H), 2.51 (s, 3H), 5.61 (br.s, 2H), 8.25 (s, 1H)

EXAMPLE 9

4-4-(Isopropyl)isoxazol-5-yl]-3-methyl-5-(methylthio) -thiophene-2-carboxamide

According to the process as stated in Example 1 except for using 6-methyl-2,4-nonanedione instead of the 2,4-hexanedione as a starting material, the title compound was prepared as colorless crystals.

Melting point: 111.5–112.5° C.

(Recrystallization solvent: Diethyl ether)

EXAMPLE 10

4-(4-Phenylisoxazol-5-yl)-5-methylthio-3-(1-propyl)-thiophene-2-carboxamide

According to the process as stated in Example 1 except for using 1-phenyl-2,4-pentanedione instead of the 2,4-hexanedione as a starting material, the title compound was prepared as colorless crystals.

Melting point: 140.0–141.0° C.

(Recrystallization solvent: Diethyl ether)

EXAMPLE 11

3,3-Dimethyl-4-(isoxazol-5-yl)-5-(methylthio) thiophene-2-carboxamide a) Ethyl 4-acetyl-3-methyl-5-(methylthio)thiophene-2-carboxylate According to the process as stated in Example 1-a) except for using 2,4-pentanedione as a starting material instead of the 2,4-hexanedione used in Example 1, ethyl 4-acetyl-3-methyl-5-(methylthio)thiophene-2-carboxylate was prepared as colorless crystals.

Melting point: 76–77° C.

(Recrystallization solvent: Diethyl ether - n-hexane)

b) Ethyl 3-methyl-5-methylthio-4-(3-oxobutyryl)thiophene-2-carboxylate

To a suspension containing 60% sodium hydride (0.64 g, 15.9 mmol) and ethyl acetate (8.16 g, 92.9 mmol) in tetrahydrofuran (5 ml) were added in turn at room temperature a solution containing ethyl 4-acetyl-3-methyl-5-(methylthio)thiophene-2-carboxylate (2.0 g, 7.7 mmol) and ethanol (0.5 ml) in tetrahydrofuran (10 ml) and a solution containing dibenzo-18-crown-6 ether (0.04 mg) in tetrahydrofuran (5 ml), and the mixture was heated under reflux for 2 hours. The reaction solution was allowed to cool down to room temperature, made acidic by addition of 3N hydrochloric acid and extracted with ethyl acetate. The organic layer was washed (with water and saturated aqueous sodium chloride, in turn), dried (over anhydrous magnesium sulfate) and concentrated under reduced pressure. The residue thus obtained was purified by silica gel column chromatography (developing solvent: n-hexane/ethyl acetate=20:1) to afford ethyl 3-methyl-5-methylthio-4-(3-oxobutyryl)thiophene-2-carboxylate (1.91 g, 82%) as yellow -crystals.

Melting point: 51–52° C.

c) 3,3'-Dimethyl-4-(isoxazol-5-yl)-5-(methylthio) thiophene-2-carboxylic acid

To ethyl 3-methyl-5-methylthio-4-(3-oxobutyryl) thiophene-2-carboxylate (1.13 g, 3.76 mmol) were added pyridine (11 ml) and hydroxyamine hydrochloride (0.29 g, 4.14 mmol) and the mixture was heated at 80° C. for one hour with stirring. The reaction solution was cooled, diluted with water and extracted with diethyl ether. The organic layer was washed (with water, 3N hydrochloric acid and saturated aqueous magnesium chloride, in turn), dried (over anhydrous magnesium sulfate) and concentrated under reduced pressure. To the resultant residue dissolved in a tetrahydrofuran-ethanol (1:1) solution (7.4 ml) was added a 20% aqueous sodium hydroxide solution (3.7 ml) at room temperature and the mixture was heated at 80° C. with stirring for one hour.

The reaction solution was allowed to cool down to room temperature, made acidic by addition of 3N hydrochloric acid and the precipitate was recovered by filtration and washed with water. The crude crystals thus obtained were dissolved in tetrahydrofuran (200 ml), dried (over anhydrous magnesium sulfate) and concentrated under reduced pressure. The residue thus obtained was recrystallized from diethyl ether-n-hexane to afford 3,3'-dimethyl-4-(isoxazol-5-yl)-5-(methylthio)thiophene-2-carboxylic acid (0.90 g, 88%) as yellow crystals.

Melting point: 248.0–249.0° C.

d) 3,3'-Dimethyl-4-(isoxazol-5-yl)-5-(methylthio)thiophene -2-carboxamide

Amidation was carried out according to the process stated in Example 1-c) to afford the title compound as pale yellow to colorless needles.

Melting point: 208.5–209.0° C.

(Recrystallization solvent: Tetrahydrofuran - n-hexane)

EXAMPLE 12

4-(Isoxazol-5-yl)-5-methylthio-3,3',N-trimethylthiophene-2-carboxamide

Amidation was carried out according to the process stated in Example 1-c) except for using a 40% aqueous solution of methylamine instead of the 25% aqueous ammonia to afford the title compound as colorless crystals.

Melting point: 98–99.5° C.

(Recrystallization solvent: Diethyl ether)

EXAMPLE 13

3,4'-Dimethyl-N-(1-hexyl)-4-(isoxazol-5-yl)-5-(methylthio)-thiophene-2-carboxamide Amidation was carried out according to the process stated in Example 1-c) except for using n-hexylamine instead of the 25% aqueous ammonia to afford the title compound as a colorless oily substance.

NMR (200 MHz, CDCl$_3$) δ: 0.90 (t, 3H, J=6.6Hz), 1.21–1.65 (m, 8H), 1.99 (s, 3H), 2.30 (s, 3H), 2.49 (s, 3H), 3.43 (dq, 2H, J=6.6Hz, 1.6Hz), 5.75 (br.s, 1H), 8.23 (s, 1H)

EXAMPLE 14

4-(Isoxazol-5-yl)-5-methylthio-3,3', N,N-tetramethyl-thiophene-2-carboxamide

Amidation was carried out according to the process stated in Example 1-c) except for using a 50% aqueous solution of dimethylamine instead of the 25% aqueous ammonia to afford the title compound as a colorless oily substance.

NMR (200MHz, CDCl$_3$) δ: 2.01 (s, 3H), 2.07 (s, 3H), 2.46 (s, 3H), 3.11 (s, 6H), 8.22 (s, 1H)

EXAMPLE 15

3,4'-Dimethyl-4-(isoxazol-5-yl)-5-(methylsulfinyl)thiophene-2-carboxamide

To a solution containing 3,4'-dimethyl-4-(isoxazol-5-yl)-5-(methylthio)thiophene-2-carboxamide (0.10 g, 0.37 mmol), which is the compound as prepared according to the process of Example 1, in dichloromethane (3 ml) was added gradually under ice-cooling m-chloroperbenzoic acid (0.07 g, 0.41 mmol) and the mixture was stirred at that temperature for 30 minutes. The reaction solution was washed (with saturated aqueous sodium hydrogencarbonate), dried (over anhydrous magnesium sulfate) and concentrated under reduced pressure. The residue thus obtained was purified by silica gel column chromatography (developing solvent: ethyl acetate) and recrystallized from ethyl acetate-n-hexane to afford 3,4'-dimethyl-4-(isoxazol-5-yl)-5-(methylsulfinyl)thiophene-2-carboxamide (0.064 g, 61%) as colorless crystals.

Melting point: 152.0–153.0° C.

EXAMPLE 16

3,4'-Dimethyl-4-(isoxazol-5-yl)-5-(methylsulfonyl)thiophene-2-carboxamide

To a solution containing 3,4'-dimethyl-4-(isoxazol-5-yl)-5-(methylthio)thiophene-2-carboxamide (0.10 g, 0.37 mmol), which is the compound as prepared according to the process of Example 1, in dichloromethane (3 ml) was added gradually at room temperature m-chloroperbenzoic acid (0.14 g, 0.81 mmol) and the mixture was stirred for 4 hours. The reaction solution was washed (with saturated aqueous sodium hydrogencarbonate), dried (over anhydrous magnesium sulfate) and concentrated under reduced pressure. The residue thus obtained was recrystallized from ethyl acetate-n-hexane to afford 3,4'-dimethyl-4-(isoxazol-5-yl)-5-(methylsulfonyl)thiophene-2-carboxamide (0.081 g, 73%) as colorless crystals.

Melting point: 182.0–183.0° C.

Test Example 1

The compounds of the present invention were determined for an enhancing activity for the induction of alkaline phosphatase production in osteoblasts derived from the parietal bone of rat fetus. Enhancing activities for the induction of alkaline phosphatase production at a concentration of the test compound of 2.5 μg/ml were 195% for Example 1, 155% for Example 3, 187% for Example 7 and 134% for Example 9, respectively, when compared with those activities without the test compounds.

Test Example 2

The compounds of the invention were determined for an enhancing activity for the nodule induction in osteoblasts derived from the parietal bone of rat fetus. Results were 342% at 1.0 μg/ml for Example 1, 501% at 2.5 μg/ml for Example 3, 576% at 2.5 μg/ml for Example 7 and 550% at 2.5 μg/ml for Example 9, respectively.

Industrial Applicability

The present invention can provide a low molecular compound which is useful for the treatment or prevention of various bone diseases or nerve diseases by specifically enhancing the action of the cell differentiation induction factors present in vivo. Specifically stated, the compound of the invention is useful as a prophylactic or therapeutic agent for osteoporosis or as an enhancing agent for osteogenesis in repairing or transplanting bone or alveolar bone.

What is claimed is:

1. A substituted isoxazolylthiophene compound represented by the formula

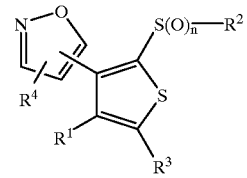

wherein $R^1$ and $R^2$ individually represent an alkyl group of 1–5 carbon atoms, $R^3$ represents a cyano group or a group a $CONR^5R^6$ (in which $R^5$ and $R^6$ individually represent a hydrogen atom or an alkyl group of 1–10 carbon atoms), $R^4$ represents an alkyl group of 1–5 carbon atoms or a phenyl group, and n is an integer of 0–2, or a salt thereof.

2. A pharmaceutical composition which comprises as an active ingredient a compound or salt thereof as claimed in claim 1.

3. An enhancing agent for the action of cell differentiation induction factors which comprises as an active ingredient a compound or salt thereof as claimed in claim 1.

4. A method of enhancing the activity of cell differentiation induction factors in a mammal comprising administering to said mammal a compound or salt thereof as claimed in claim 1.

\* \* \* \* \*

UNITED STATES PATENT AND TRADEMARK OFFICE
CERTIFICATE OF CORRECTION

PATENT NO.    : 6,355,663 B1
DATED         : March 12, 2002
INVENTOR(S)   : Harada et al.

It is certified that error appears in the above-identified patent and that said Letters Patent is hereby corrected as shown below:

Column 9,
Line 46, delete "10"

Column 11,
Lines 18-19, delete "3-Ethyl-4-(4-methylisoxazol-5-yl)-5-(methylthio)thiophene-2-carboxamide"
Line 19, "Etkylisoxazol" should read -- Ethylisoxazol --
Line 30, "4-(1-Butyl)" should read -- 4-[4-(1-Butyl) --

Signed and Sealed this

Twenty-fourth Day of September, 2002

Attest:

JAMES E. ROGAN
Attesting Officer        Director of the United States Patent and Trademark Office